US00PP28357P3

(12) United States Plant Patent
Mazzardis

(10) Patent No.: US PP28,357 P3
(45) Date of Patent: Sep. 5, 2017

(54) BLUEBERRY PLANT NAMED 'EB 8-50'

(50) Latin Name: ***Vaccinium* hybrid**
Varietal Denomination: EB 8-50

(71) Applicant: Vincent David Mazzardis, Joondalup (AU)

(72) Inventor: Vincent David Mazzardis, Joondalup (AU)

(73) Assignee: Bisa Trading Pty. Ltd., Cannington (AU)

( * ) Notice: Subject to any disclaimer, the term of this patent is extended or adjusted under 35 U.S.C. 154(b) by 20 days.

(21) Appl. No.: 14/756,639

(22) Filed: Sep. 28, 2015

(65) Prior Publication Data

US 2016/0113169 P1 Apr. 21, 2016

(30) Foreign Application Priority Data

Oct. 16, 2014 (AU) ..... 2014/242

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

FOREIGN PATENT DOCUMENTS

AU 2014/24 10/2014

OTHER PUBLICATIONS

Plant Varieties Journal, vol. 28, No. 1; published Jun. 15, 2015.

*Primary Examiner* — Susan McCormick Ewoldt
(74) *Attorney, Agent, or Firm* — Randall Danskin P.S.

(57) ABSTRACT

A new and distinct variety of blueberry plant is disclosed and which is denominated varietally as 'EB 8-50', and which further produces a large to very large fruit which is mature for harvesting and shipment in the early season under the ecological conditions prevailing in Yanchep Springs, Western Australia.

1 Drawing Sheet

Latin name: '*Vaccinium* Hybrid'.
Varietal denomination: 'EB 8-50'.

RELATED APPLICATION DATA

The present application claims priority to Australian Plant Breeders Right Application, Serial No. 2014/242, and which was filed on Oct. 16, 2014, and which further was accepted on Dec. 23, 2014.

BACKGROUND OF THE NEW VARIETY

The present invention relates to a new, novel and distinct variety of blueberry plant '*Vaccinium* hybrid', and which has been denominated varietally hereinafter as 'EB 8-50'.

ORIGIN

The present variety of blueberry plant resulted from an ongoing development program which I have conducted to identify such plants. The purpose of this program is to improve the commercial quality of blueberry plants, and other plant species. To this end, I have made controlled, hybrid, cross-pollinations in order to produce plant populations from which improved progenies are evaluated, and thereafter selected.

The blueberry plant, 'EB 8-50', was originated by me, and selected from a population of new plants growing at my farm, and which is located near Yanchep Springs in Yanchep, Western Australia. The new variety of blueberry plant was derived from a controlled cross-pollination of a seed parent, blueberry plant '03-2' [unpatented]; and a pollen parent, blueberry plant 'SB-1' [unpatented], during the 2005 growing season. The seed parent is characterized principally by a semi-upright, bush-type growth habit, and which further has a mid-season flowering date; and further produces medium to large sized, and firm fruit. On the other hand, the pollen parent is characterized by a semi-upright growth habit; an early season flowering date; and further produces a large sized fruit. The resulting seed derived from the seed parent, as noted above, produced approximately 500 plants. The fruit of these new plants were first assessed during the 2007 growing season. A further assessment was conducted in 2008. At that time the new variety 'EB 8-50' was selected for further asexual propagation. Subsequent evaluations of the plant growth habits and the fruit produced by these other asexually produced plants has convinced me that the present variety, 'EB 8-50', is indeed new and novel. As should be understood, additional asexual propagations and evaluations occurred during the 2009 through 2014 growing seasons. The present, new variety of blueberry plant is considered to be novel in view of its semi-upright bush-type growth habit; the production of a large to very large, and round fruit which has an excellent flavor, and which further displays an early flowering and fruit maturity dates. The fruit of the present variety typically displays a small, dry picking scar. In relative comparison to the seed parent, blueberry plant '03-2', the new variety of blueberry plant is clearly distinguishable based upon its production of large to very large sized fruit. In contrast, the seed parent, blueberry plant '03-2', produces what is considered to be a medium-large sized fruit. Still further, the seed parent is distinguishable from the present variety because of its mid-season date for the beginning of flowering on one-year-old and current year shoots. In contrast, the present variety has a beginning date of flowering on one-year-old and older shoots which is considered to be very early in the season. With respect to the pollen parent 'SB-1' the present variety is distinguishable because of it's large to very large fruit size in relative comparison to size of the fruit which is produced by the pollen parent, blueberry plant 'SB-1'. Still further, the pollen parent 'SB-1' is distinguishable from the new variety in view of the later flowering date on current years shoots in view of the very early date of flowering which is expressed by the new variety. The asexual reproduction of Blueberry Plant EB 8-50 occurred at Yanchep Springs, Yanchep Western Australia.

In relative comparison to the closest-known varieties, the inventor has identified the blueberry varieties 'EB 8-1'; the 'Sharp Blue'; and the 'Ridley 1111' blueberry plants, as the varieties that are most closely similar to the present variety. With respect to blueberry plant 'EB 8-1', which is further identified as U.S. Plant Pat. No. 25,859, and which was filed on Jun. 12, 2015, the present, new variety of blueberry plant is distinguishable therefrom by its growth habit; calyx basin depth; sepal type; fruit firmness; fruit sweetness and acidity. With respect to the blueberry variety, 'Sharp Blue' [unpatented], the present, new variety is distinguishable therefrom by producing a semi-upright growth habit as opposed to the bushy spreading growth habit expressed by the 'Sharp Blue' blueberry plant. The 'Sharp Blue' blueberry plant is also distinguishable from the present variety because the present variety produces a large to very large fruit as opposed to the average to large sized fruit produced by the 'Sharp Blue' blueberry plant. With respect to the blueberry plant 'Ridley 1111', which is further identified as U.S. Plant Pat. No. 25,572, this blueberry plant is distinguishable from the present, new variety, because the new variety of blueberry plant produces a large to very large fruit, as opposed to the medium to large sized fruit produced by the 'Ridley 1111' blueberry plant. It should be understood that the asexual propagation of the present, new blueberry plant was accomplished by means of cuttings. My observations of the new and novel plant over a number of years has confirmed that the plant characteristics of the present, new variety of blueberry plant has remained true across multiple generations to those characteristics which were first observed in the original cross-pollinated plant.

BRIEF DESCRIPTION OF THE DRAWINGS

The accompanying drawing which is provided is a color photograph of the new blueberry plant EB 8-50, at an age of two (2) years, juxtaposed relative to an image of the closest known variety 'EB 8-1' (U.S. Plant Pat. No. 25,859). The photograph shows a vegetative stem bearing typical leaves, and several fruit produced by the new variety of blueberry plant, sufficiently matured for harvesting and shipment. Similarly, the comparator variety, blueberry plant 'EB 8-1' is shown adjacent to the photograph showing the new variety, 'EB 8-50'. Again, this image shows a twig bearing typical leaves, one leaf showing the dorsal coloration thereof, and several fruit of the comparator variety sufficiently matured for harvesting and shipment. The color in this photograph is as nearly true as is possible in a color representation of this type. Due to chemical development, processing, and printing, the leaves and fruit depicted in this photograph may, or may not be accurate when compared to the actual specimen. For this reason, future color references should be made to the color plates, and the descriptions as provided hereinafter. Common color names are also occasionally employed.

NOT A COMMERCIAL WARRANTY

The following detailed descriptions were prepared to solely comply with the provisions of 35 U.S.C. §112, and do not constitute a commercial warranty, [either expressed or implied], that the present variety will, in the future, display the botanical, horticultural or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present new variety.

The age of the plant at the time of the description that follows herein is three (3) years.

The colors and codes used herein to describe the EB 8-50 Blueberry plant, refer to The Royal Horticultural Society (R.H.S.) Colour Chart, 5$^{th}$ Ed., 2007.

Plant:

*Plant vigor.*—Considered average for the species.

*Plant growth habit.*—Semi-upright to intermediate in its growth habit. This is in contrast to the closest known variety 'EB 8-1', and which is considered to have a semi-spreading growth habit. Still further, and in contrast to the seed parent, blueberry plant '03-2', the seed parent displays a semi-upright bush-type growth habit; and the pollen parent 'SB-1' has a semi-upright growth habit.

*Color, one year old shoots.*—Yellow Green N144C (R.H.S. Colour Chart, 5$^{th}$ Ed. 2007).

*Internode length.*—One Year Old Shoots — Medium to long for the species, about 10.7 mm. Height of plant at time of description is about 1.2 m. Width of plant at time of description is about 1.1 m. Bark Color is Greyed Orange. 177C (R.H.S. Colour Chart, 5$^{th}$ Ed., 2007).

Leaves:

*Leaf length.*—Considered average for the species. The average leaf length is about 63.73 millimeters.

*Leaf width.*—Considered average for the species. The average leaf width is about 32.85 millimeters.

*Ratio of leaf length vs. leaf width.*—Considered small. This is in relative comparison to the closest known variety 'EB 8-1', and where this ratio is considered to be average.

*Leave shape.*—Considered ovate.

*Leaf color.*—Dorsal Surface — Yellow Green 146A (R.H.S. Colour Chart, 5$^{th}$ Ed., 2007).

*Leaf color.*—Under Surface is Yellow Green 147B (R.H.S. Colour Chart, 5$^{th}$ Ed., 2007).

*Texture of the leaf.*—Glabrous.

*Leaf apex shape.*—Acute.

*Leaf apex base shape.*—Acute to obtuse.

*Vein color of the leaf is.*—Yellow Green 144D (R.H.S. Colour Chart, 5$^{th}$ Ed., 2007).

*Venation pattern of the leaf.*—Pinnately reticulate.

*Leaf arrangement.*—Alternate.

*Intensity of leaf color.*—Dorsal Surface — Dark green. This color, on occasion, is noticeably darker than the dorsal coloration of the leaves as seen on the closest known variety 'EB 8-1'.

*Leaf marginal edge.*—Generally — Entire. Seed Color is Greyed Orange 168C (R.H.S. Colour Chart, 5th Ed., 2007).

Flowers:

*Flower bud coloration.*—Generally speaking, the anthocyanin coloration is considered very weak.

*Inflorescence length.*—Considered average for the species, about 23.6 mm.

*Color of opened flower.*—White 155C (R.H.S. Colour Chart, 5th Ed., 2007). Average number of flowers per inflorescence if Five (5).

*Corolla texture.*—Rigid. Corolla length is about 10 mm. Corolla diameter is about 8.07 mm.

*Corolla color.*—White 155C (R.H.S. Colour Chart, 5th Ed., 2007). Corolla aperture size is about 3.5 mm. Pedicle length is about 7.6 mm.

*Pedicle color.*—Yellow Green 145B (R.H.S. Colour Chart, 5th Ed., 2007). Date of bloom time is about May-June in the specified location of culture. Duration of bloom time is about 6-8 weeks in the specified location of culture.

*Corolla shape.*—Urceolate.

*Corolla tube size.*—Considered average for the species.

*Corolla tube coloration.*—Generally — The anthocyanin coloration is considered to be absent or very weak.

*Corolla tube ridges.*—Present.

Fruit:

*Fruit cluster density.*—Considered dense for the species.

*Intensity of green coloration.*—Unripe Fruit — Yellow Green 145C (R.H.S. Colour Chart, 5th Ed., 2007).

*Fruit size.*—Generally speaking, the new variety is considered to produce large to very large fruit which have an average size of about 20.92 mm. This in contrast to the merely large fruit size which is produced by the closest known variety blueberry plant 'EB 8-1'. In this regard, the average fruit height is about 16.75 millimeters. This is in contrast to the closest known variety 'EB 8-1', and which has an average height of about 14.78 mm.

*Fruit weight.*—On average, about 5.04 grams. This is in contrast to the closest known variety 'EB 8-1' and which has an average fruit weight of about 4 grams.

*Fruit shape.*—When viewed in a longitudinal section, the fruit shape is considered round. This is in contrast to the same fruit characteristic as seen in the closest known blueberry variety 'EB 8-1', and which is considered oblate.

*Sepal position.*—Attitude — Erect.

*Sepal type.*—Generally — Reflexed. This is in contrast to the same plant characteristic as displayed in the blueberry variety 'EB 8-1', and which is considered to be straight.

*Calyx basin diameter.*—Considered very small, about 6.42 mm. Further, the calyx basin depth is on average about 1.55 millimeters, and is further considered very shallow to shallow. This is in contrast to the closest known variety 'EB 8-1' and where the same characteristic is expressed as an average depth of about 2.90 millimeters.

*Fruit.*—Intensity of Bloom — Considered very strong. On the other hand, the variety 'EB 8-1' has only a strong bloom.

*Fruit skin color.*—Black 203D (R.H.S. Colour Chart, 5th Ed., 2007).

*Fruit flesh color (ripened fruit).*—Green White 157D (R.H.S. Colour Chart, 5th Ed., 2007).

*Fruit firmness.*—Firm to very firm for the species. This is in contrast to the average firmness as displayed by the fruit produced by the closest known blueberry variety 'EB 8-1'.

*Fruit sweetness.*—Considered high to very high for the species. This is in contrast to the fruit produced by the blueberry plant 'EB 8-1', and where the fruit sweetness is considered to be merely average.

*Fruit acidity.*—Considered low for the species. This is in contrast to the average acidity as expressed by the fruit which is produced by the variety 'EB 8-1'.

*Plant.*—Fruit Type — Fruiting occurs on one-year-old, and current season's shoots.

*Resistance to insects and disease.*—No particular acceptabilities were noted. The present variety has not been tested to expose or detect any susceptibilities or resistance to any known plant and/or fruit diseases.

*Reproductive organs of the plant.*—Size of the pollen anthers is about 4.2 mm. Color of the pollen anthers is Greyed Orange 167B (R.H.S. Colour Chart, 5th Ed., 2007). Pistil length is about 6 mm. Pistil color is Yellow Green 145B (R.H.S. Colour Chart, 5th Ed., 2007). Market use of the fruit is First Grade Fresh Market Fruit.

*Pollination requirement.*—Self-fertile.

*Fruit productivity.*—Average weight of fruit is about 5.04 g. Storability of the plant fruit is considered to be long. The observed date of the first pick is approximately September in the specified location of culture. The observed date of the last pick is approximately December in the specified location of culture. Although the new variety of blueberry plant possesses the described characteristics when grown under the ecological conditions prevailing near Yanchep Springs, Western Australia, it should be understood that variations of the usual magnitude, and characteristics incident to changes in growing conditions, fertilization, pruning, pest control, frost, climatic variables, and horticultural management are to be expected.

Having thus described and illustrated my new variety of blueberry plant, what I claim is new, and desire to secure by plant Letters Patent is:

1. A new and distinct variety of blueberry plant, substantially as illustrated and described, and which is characterized as to novelty by producing a relatively large to very large fruit, and which is further mature for harvesting and shipment in the very early season under the ecological conditions prevailing near Yanchep Springs, Western Australia.

* * * * *

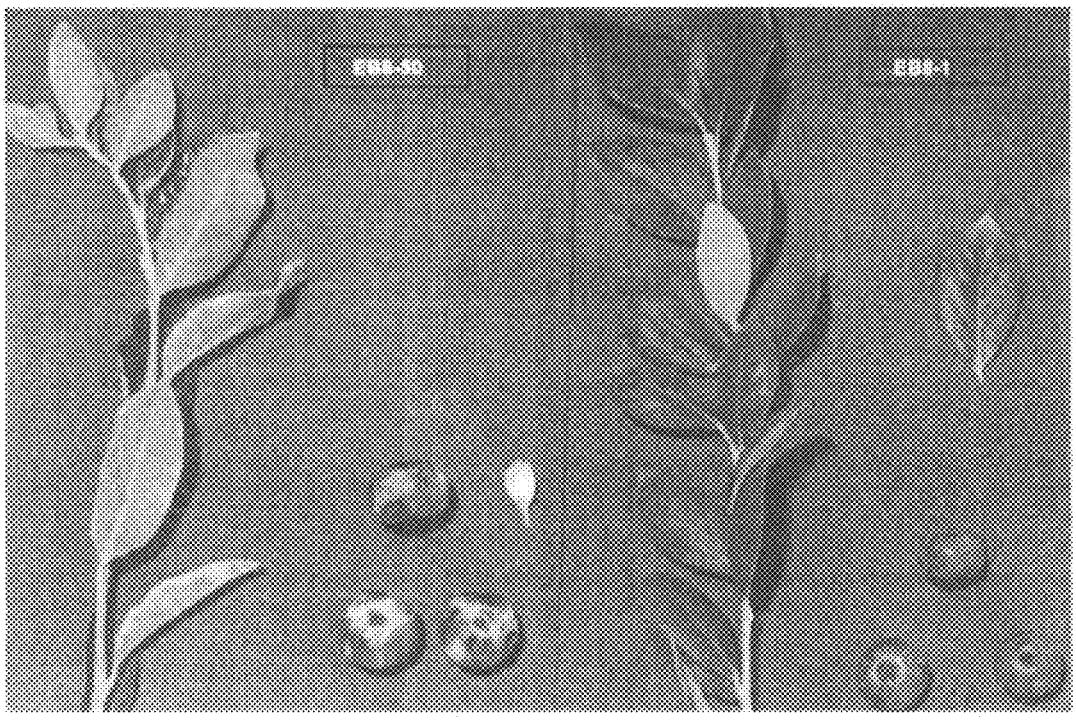
FHL-56
BBH-1